United States Patent [19]

Bechara

[11] Patent Number: 4,467,089
[45] Date of Patent: Aug. 21, 1984

[54] CARBAMATE AND CARBONATE SALTS OF TERTIARY AMINES

[75] Inventor: Ibrahim S. Bechara, Boothwyn, Pa.

[73] Assignee: Air Products and Chemicals, Inc., Allentown, Pa.

[21] Appl. No.: 354,844

[22] Filed: Mar. 4, 1982

[51] Int. Cl.³ .................. C07D 295/20; C07D 295/02; C07D 487/08; C07D 233/10

[52] U.S. Cl. .................. 544/351; 260/501.2; 260/501.1; 562/550; 564/508; 528/49; 544/178; 544/172; 548/347; 502/167

[58] Field of Search .................. 544/351, 352; 564/508

[56] References Cited

U.S. PATENT DOCUMENTS

| | | | |
|---|---|---|---|
| 3,655,719 | 4/1972 | Anderson | 544/351 |
| 3,728,291 | 4/1973 | Carroll et al. | 260/2.5 |
| 3,767,602 | 10/1973 | Carroll | 521/115 |
| 3,839,252 | 10/1974 | Bosso et al. | 528/219 |
| 3,962,100 | 6/1976 | Murphy et al. | 252/8.8 |
| 4,102,863 | 7/1958 | Buchwalter et al. | 525/523 |
| 4,141,810 | 2/1979 | Buchwalter et al. | 525/121 |

OTHER PUBLICATIONS

Daimer et al., I Chem. Abs. 90, 170268(1979).

Daimer et al., II Chem. Abs. 90, 40,320(1978).

*Primary Examiner*—Mark L. Berch
*Attorney, Agent, or Firm*—Michael Leach; E. Eugene Innis; James C. Simmons

[57] ABSTRACT

Novel carbamic and carbonic acid derivatives are provided by simultaneous reaction of a secondary amine and a tertiary amine with carbon dioxide. These derivatives correspond in general to the formula

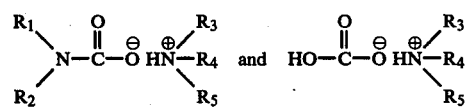

in which $R_1$ and $R_2$ may be individual substituents attached to the N or together form with N a heterocyclic moiety; $R_3$, $R_4$, $R_5$ may be individual short chain alkyl or hydroxyalkyl substituents on the N or form therewith a monocyclic or bicyclic heterocyclic moiety. These described compounds find particular use as heat activatable delayed action catalysts especially for use in polyurethane formulations.

2 Claims, No Drawings

CARBAMATE AND CARBONATE SALTS OF TERTIARY AMINES

BACKGROUND OF THE INVENTION

The present invention relates to the composition and synthesis of novel carbonic and carbamic acid derivatives, particularly tertiary amine salts of substituted carbamic and carbonic acids, and to their use particularly as delayed action urethane catalysts.

Carbamic acid, also sometimes designated as aminoformic acid, is not known in the free state. Salts of carbonic acid as well as certain esters thereof are known, including among these metal salts, the ammonium salt, and alkyl esters (urethanes).

Ammonium carbamate has been prepared by reaction of dry ice and liquid ammonia. The preparation of certain alkyl ammonium carbamates, stated to be useful as softening and anti-static agents for fabrics are disclosed in U.S. Pat. No. 3,962,100. The therein disclosed carbamate compounds are prepared by dissolving a primary or secondary long chain alkyl amine in an alcohol solvent and bubbling carbon dioxide through the solution or by reaction of the amine with solid $CO_2$. The obtained compounds correspond to the general formula:

wherein $R_1$ is hydrogen or alkyl, $R_2$ is a long chain alkyl group, $R_3$ and $R_4$ each is hydrogen or alkyl.

The use of tertiary amine compounds as catalysts and/or co-catalysts in the promotion of isocyanate reactions such as in the preparation of polyurethanes, is well known and certain of these are extensively employed in industry; as for example triethylenediamine, also known as diazabicyclo (2.2.2) octane. Triethylenediamine and other tertiary amine catalysts have also been used or proposed for use in the form of their salts combined with carboxylic acids, so as to stabilize the amine in certain stored compositions or to delay the catalytic effect of the amine in use. See for example, U.S. Pat. No. 3,767,602, which discloses the use of formates and acetates of certain tertiary amine catalysts; including, in addition to such salts of triethylenediamine and methyltriethylenediamine, those of dimethylaminoethyl morpholine, bis-(dimethylaminoethyl) ether, hydroxypropylimidazole, tetramethylbutylenediamine.

Mixtures of the diformate salt of triethylenediamine and hydroxypropyl imidazole in combination with tin catalysts such as tin octoate are known to be useful as delayed action catalysts (DAC), i.e. those which initially delay and then catalyze the polyurethane reactions; see U.S. Pat. No. 3,728,291. Such DAC catalysts extend the cream time to permit the polyurethane reaction to penetrate the intricate parts of the mold and to extend the gelation time as the resulting foam on gelling becomes intractable and resists molding, but to rapidly catalyze the subsequent polymerization rate so that the rise and cure times are comparable to non-DAC catalysts.

SUMMARY OF THE INVENTION

In accordance with the present invention there are provided certain tertiary amine salts of N-substituted carbamic acid and of carbonic acid which, among other possible useful applications, have particular utility as thermally activatable catalysts for polyurethane production and for curing of epoxies. The novel compounds of the invention correspond to the following general structural formula:

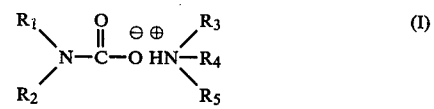

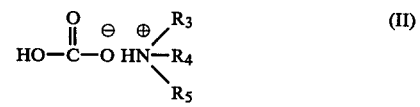

where $R_1$ and $R_2$ can independently be alkyl groups of 1 to 20 carbon atoms, which alkyl groups may contain one or more hydroxyl groups, or $R_1$ and $R_2$ together can be a carbon atom containing chain joined to N to form a hetero ring, such as for example imidazole, morpholine, piperazine, and the like. $R_3$, $R_4$ and $R_5$ can independently be alkyl groups of 1 to 3 carbons, hydroxy alkyl groups of up to 3 carbons, or they can be organic radicals joined wherein $R_3$ and $R_4$ or $R_3$ and $R_5$ can be joined to form a monocyclic or bicyclic hetero ring comprising tertiary nitrogen, such as in triethylene diamine, quinuclidine, N-alkyl piperazine, N-alkyl morpholine, and the like. In addition, one of these R groups can be an ethylene radical attached to another dialkylamino alkyl group by oxygen to form a ditertiary amine of the formula:

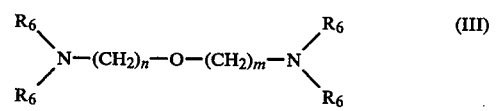

where each of the $R_6$ substituents is an alkyl group of up to 3 carbon atoms; n and m are independently 2 or 3.

Compounds of formula I or II are prepared by reacting a non-hindered tertiary amine in aqueous or glycolic solvent with carbon dioxide in the presence or absence of secondary amine according to the following reactions:

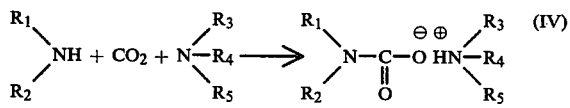

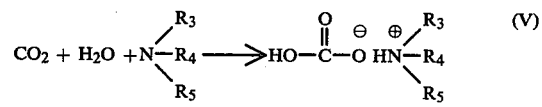

The compounds of the invention are characterized either by having at one end a secondary amine moiety and at the other a tertiary amine salt of the carbamic acid, or by a tertiary amine salt of the carbonic acid. Upon being heated to moderate temperatures in the order of about 50°–100° C., they decompose irreversibly with the evolution of carbon dioxide, thus freeing the tertiary amines. Because of this property, the compounds of the invention find utility as thermally activatable catalysts for polyurethane and for epoxy curing. They can also be used as blowing agents in various plastic formulations.

In the preferred reactions, the secondary and tertiary amines are brought together in equimolar proportions in the presence of excess carbon dioxide and under mild pressure of about 1-6 atmospheres. Thus, the secondary amine reacts with $CO_2$ to form the corresponding di-substituted carbonic acid, which in turn reacts with the tertiary amine to form the desired salt or alternatively the carbon dioxide reacts with water to form carbonic acid which is trapped by the tertiary amine to yield the amine salt of carbonic acid.

DETAILED DESCRIPTION

Illustrative of the novel carbamate compounds of the invention, although not limited thereto, are the following, prepared by reaction of a secondary and tertiary amine with $CO_2$:

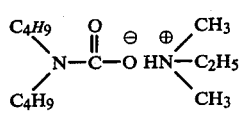
(VI)

prepared by reaction of $CO_2$ with dibutyl amine and ethyldimethyl amine;

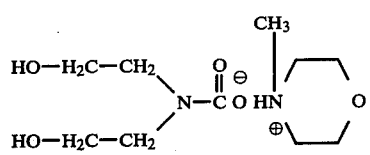
(VII)

from diethanolamine and N-methyl morpholine;

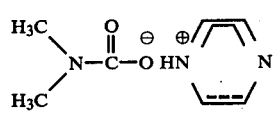
(VIII)

from dimethyl amine and triethylamine diamine (TEDA);

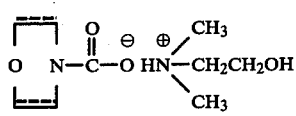
(IX)

from morpholine and dimethyl ethanolamine;

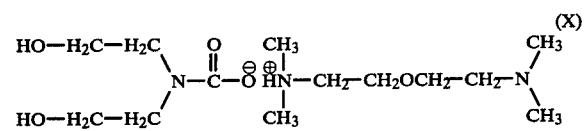
(X)

from diethanolamine and bis (N,N'-dimethylamino)-ethyl ether.

Illustrative examples of the novel carbonate compounds of this invention, although not limited thereto, are the following in which water, carbon dioxide and a tertiary amine are reacted as indicated below:

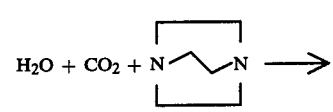
(XI)

(TEDA)

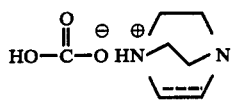

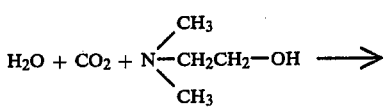
(XII)

(dimethyl ethanol amine)

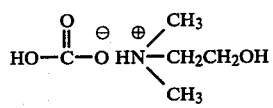

(XIII)

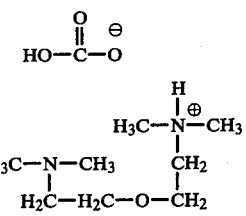

(bis(dimethylamino ethyl) ether)

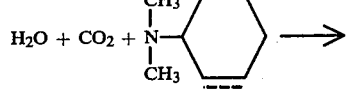
(XIV)

(dimethyl cyclohexyl amine)

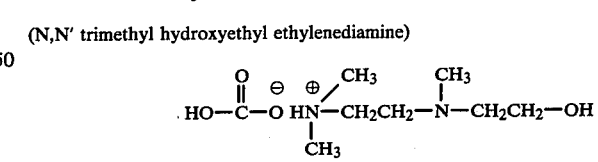
(XV)

(N,N' trimethyl hydroxyethyl ethylenediamine)

EXAMPLE 1

Into a round bottomed flask there was charged 400 parts by weight of diethylene glycol solvent, 105 parts of diethanol amine and 112 parts of triethylenediamine (equimolar parts of reactants). The mixture was stirred until complete solution was obtained. A $CO_2$ generating device (dry ice in an Erlenmeyer flask) was then connected to the stirring reaction mixture and $CO_2$ allowed to bubble in for one day under pressure of 200 ml of water. At the end of this period the flask containing the reaction mixture was weighed and a weight gain of 36 parts was noted, due to the reacted $CO_2$.

The product was analyzed by nuclear magnetic resonance (NMR) spectroscopy. The NMR analysis showed the product of Example 1 to contain the carbamic acid salt of triethylenediamine and diethylene glycol. The analysis as shown in Table I was carried out at ~25° C. using $D_2O$ as the solvent.

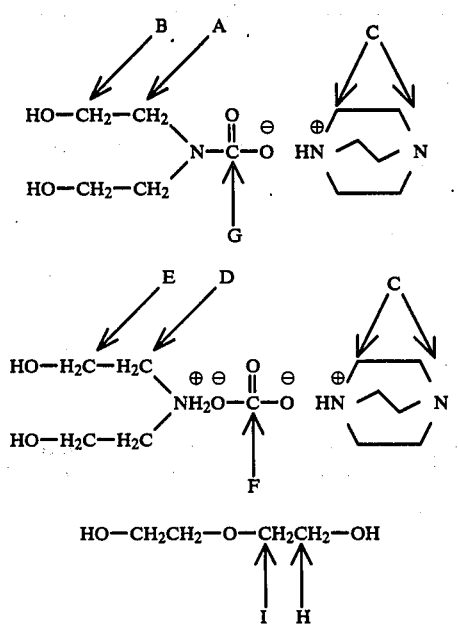

TABLE I

NMR Analysis of Product From Example 1

| Proton/ Carbon | H'NMR Chemical Shift, ppm (Multiplicity) | $C^{13}$ NMR Chemical Shift, ppm | Integration (area) |
|---|---|---|---|
| A | 3.25 (triplet overlaps H & I) | 51.2 | 2.0 |
| B | 3.65 (triplet overlap H & I) | 61.7 | 2.5 |
| C | 2.83 (singlet) | 4.5 | 12.7 |
| D | 2.85 (triplet overlaps C) | 50.2 | 2.2 |
| E | 3.5 (triplet) | 58.5 | 2.0 |
| F | — | 161 | 1.0 |
| G | — | 163.8 | 2.0 |
| H | 3.6–3.9 (overlap A & B) | 61 | 8.6 |
| I | 3.6–3.9 (overlap A & B) | 72.5 | 8.6 |

NMR Analysis shows that the product is a mixture of the carbamate and carbonate salts of triethylenediamine. The ratio of carbamate to carbonate is about 2/1.

EXAMPLES 2–4

Into a round bottomed flask equipped with a stirrer and a gas inlet tube, there was charged water and/or diethylene glycol and equimolar parts of a secondary and a tertiary amine. The flask was tared and $CO_2$ gas bubbled in. The weight of the reaction mixture was periodically checked for $CO_2$ absorption. When about an equimolar amount of $CO_2$ was absorbed, the reaction was stopped and the product analyzed by NMR. Table II below summarizes the analytical results obtained on products of Examples 2, 3, and 4.

TABLE II

NMR Analysis of Products from Examples 2–4

| Example | Solvent | Secondary Amine Used | Tertiary Amine Used | Structure of the Products Obtained | Chemical Shift, ppm | H' NMR Multiplicity | Integration | $C^{13}$ NMR Chemical Shift | Multiplicity | Integration |
|---|---|---|---|---|---|---|---|---|---|---|
| 2 | water | morpholine | TEDA | (structure shown) | A 3.25 | triplet (Overlap D) | 4.1 | Overlap C | — | — |
| | | | | | B 3.75 | triplet | 3.8 | 65.59 | — | 0.24 |
| | | | | | C 2.99 | singlet | 1.3 | 45.32 | triplet | 2.54 |
| | | | | | D 3.53 | triplet | 4.0 | Overlap C | — | — |
| | | | | | E 3.75 | triplet | 3.8 | 67.82 | — | 0.54 |
| | | | | (structure shown) | F — | — | — | 163.99 | — | 0.21 |
| | | | | | G — | — | — | 161.85 | — | 0.20 |
| 3 | DEG, water | morpholine | TEDA | (structure shown) | A 3.24 | complex | — | 44.3 | triplet | 2.7 |
| | | | | | B 3.65 | triplet | — | 66.38 | triplet | 6.77 |
| | | | | | C 2.88 | singlet | — | 45.32 | triplet | 35.52 |

TABLE II-continued
NMR Analysis of Products from Examples 2-4

| Example | Solvent | Secondary Amine Used | Tertiary Amine Used | Structure of the Products Obtained | Chemical Shift, ppm | H' NMR Multiplicity | Integration | C$^{13}$ NMR Chemical Shift | Multiplicity | Integration |
|---|---|---|---|---|---|---|---|---|---|---|
| | | | | [structure with morpholinium carbamate and HN-CH$_2$-CH$_2$-N ring, labels B, A, I, C] | D 3.6–3.7 | Complex | — | 72.44 | triplet | 21.35 |
| | | | | HO—CH$_2$CH$_2$O—CH$_2$—CH$_2$—OH (labels E, D) | E 3.5–3.7 | Complex | — | 61.13 | triplet | 21.55 |
| 3 | DEG water | morpholine | TEDA | | F 3.65 | Overlap | — | 67.36 | triplet | 7.69 |
| | | | | | G 3.5 | Overlap D & E | — | 45.09 | triplet | 5.9 |
| | | | | | H — | — | — | 163.45 | singlet | 3.22 |
| | | | | | I — | — | — | 161.13 | singlet | 0.45 |
| 4 | DPG | morpholine | bis-)di-methylamino ethyl) ether | [structure: morpholinium carbamate + CH$_3$CH$_3$N—CH$_2$—CH$_2$—O—CH$_2$CH$_2$N(CH$_3$)H, labels B, A, F, C, D, E, +S] | A 3.52 | triplet | — | 4 5 | — | — |
| | | | | | B 3.7 | (Overlap E) | — | 6 5 | — | — |
| | | | | | C 2.6 | singlet | — | 43.5 | — | — |
| | | | | [structure: morpholinium O—C(=O)—OH, labels G, I, H] | D 3.05 | triplet | — | 57.0 | — | — |
| | | | | | E 3.65 | overlaped | — | 67.0 | — | — |
| | | | | | F — | — | — | 163.2 | — | — |
| | | | | | G — | — | — | 160.3 | — | — |
| | | | | HO—CH(CH$_3$)—CH$_2$—OCH$_2$—CH(CH$_3$)—OH (labels J, K, L) | H 3.25 | triplet | — | 45 | — | — |
| | | | | | I 3.65 | triplet | — | 65 | — | — |
| | | | | | J 1.1 | doublet | — | 19 | — | — |
| | | | | [morpholine O—NH, label M] | K 3.4 } weak & diffused signals | | | | | |
| | | | | | L 3.9 | | | | | |
| | | | | | M 2.95 | triplet | — | | | |

It is evident from carbon 13 NMR shown in Table 2 above that both the carbamate and the carbonate salts of tertiary amines were formed. The amount of carbamate was greater than the carbonates by a ratio of at least 2:1.

EXAMPLES 5-7

Into a round bottomed flask equipped as in Example 1 was charged 1 mole of tertiary amine and 100-500 cc of water. The flask was connected to a carbon dioxide cylinder by means of gas inlet adaptor and rubber tubing and to a burette containing 500 cc of Nujol oil by means of gas outlet and rubber tubing. The burette of Nujol oil was used to maintain a pressure greater than atmospheric on the reaction vessel. $CO_2$ was bubbled in with stirring until a gain of 1 mole of $CO_2$ was realized. The reaction mixture was then stopped and the flask was allowed to stand at atmospheric pressure and at ambient temperature overnight. The mixture was then analyzed by NMR. The tertiary amine carbonate salts made by this method and their analysis are shown on Table III below.

EXAMPLE 8

The same apparatus was used in Examples 5-7. The flask was charged with 0.5 mole of TEDA, 0.5 mole of 2-methylimidizole, (a secondary amine of low basicity) and about 120 cc of water. Carbon dioxide was bubbled in till a gain of 22 gm (0.5 mole) was introduced. The reaction mixture was then analyzed by NMR. The product from this experiment, as shown in Table IV below was the triethylenediamine carbonate salt with free (unreacted) 2-methyl imidazole. No carbamate was formed which establishes the fact that carbamate formation requires secondary or primary amines of strong basicity.

TABLE III

NMR Analysis of Products from Examples 5-7

| Example | Solvent | Tertiary Amine Used | Structure of the Products Obtained | H' NMR Chemical Shift, ppm | Multiplicity | Integration | $C^{13}$ NMR Chemical Shift | Multiplicity | Integration |
|---|---|---|---|---|---|---|---|---|---|
| 5 | water | dimethylethanol amine | (structure) | A 2.74<br>B 3.10<br>C 3.76<br>D — | singlet<br>triplet<br>triplet<br>— | 13.2<br>4.5<br>4.3<br>— | 43.64<br>56.4<br>59.63<br>161.77 | quartet<br>triplet<br>triplet<br>singlet | 49.6<br>27.3<br>24.6<br>21.6 |
| 6 | water | N,N'—trimethyl N—hydroxyethyl ethylene diamine | (structure) | A 2.66<br>B 3.05<br>C 2.75<br>D 2.25<br>E 2.60<br>F 3.60<br>G — | singlet<br>triplet<br>triplet<br>singlet<br>triplet<br>triplet<br>— | 5.4<br>1.8<br>1.8<br>2.6<br>1.8<br>1.8<br>— | 43.8<br>58.82<br>52.25<br>41.76<br>54.87<br>58.98<br>161.14 | quartet<br>triplet<br>triplet<br>quartet<br>triplet<br>triplet<br>singlet | 7.4<br>3.2<br>3.3<br>3.3<br>3.5<br>3.2<br>3.2 |
| 7 | water | TEDA | (structure) | A 3.05<br>B — | singlet<br>— | —<br>— | 44.5<br>161.1 | triplet<br>singlet | 19.3<br>2.53 |

TABLE IV
NMR Analysis for Product of Example 8

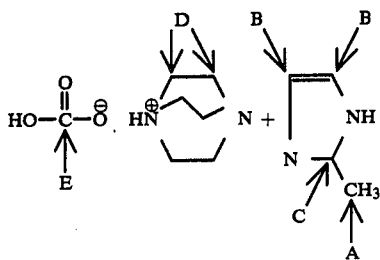

| Chem. Shift, ppm | H' NMR Multiplicity | Integration | Chem. Shift, ppm | C¹³ NMR Multiplicity | Integration |
|---|---|---|---|---|---|
| A 2.31(2.31)[a] | singlet | 1.93 | 12.81(13.7)[a] | quartet | 3.9 |
| B 6.95(6.91)[a] | singlet | 1.18 | 121.19(121.1)[a] | doublet | 7.51 |
| C — | — | — | 145.73(144)[a] | singlet | 3.73 |
| D 3.04(2.63)[b] | singlet | 8.4 | 44.97 | triplet | 23.78 |
| E — | — | — | 161.89 | singlet | 4.46 |

[a]Chemical shifts for unreacted 2-methyl/imidazole obtained from Sadtler Standards.
[b]Chemical shift for unprotonated TEDA.

EXAMPLE 9

Into a round bottomed flask fitted with a gas outlet tube and a thermometer, there was charged 50 grams of the product of Example 1. The gas outlet tube was connected by rubber tubing to a reservoir of a saturated solution of barium hydroxide. The flask was immersed in an oil bath and heated, while monitoring temperature and gas evolution. When the temperature of the solution inside the flask reached 33° C., bubbling of the gas into the barium hydroxide solution was observed. At 48° C. vigorous gas bubbling occurred with concomitant precipitation of barium carbonate, indicating that the liberated gas was carbon dioxide. When gas evolution ceased, the contents of the flask was cooled and weighed. A weight loss of 1.5 grams, or about 3% by weight of the total, was noted. The theoretical carbon dioxide content of the compound is 5% by weight. The pH of the decomposed product at 3% in distilled water and 25° C. was 9.3. The pH of a 3% solution of the undecomposed sample at 25° C. was 8.7.

From the foregoing example, it is apparent that the compounds of the present invention are thermally sensitive and decompose at about 50° C. to generate the active triethylenediamine (or other tertiary amine moiety of the starting compound) with liberation of $CO_2$, as evidenced by precipitation of barium carbonate and by the increase in the pH of the decomposed product. It is also noteworthy that the products of the present invention have a major advantage over other DAC amine catalysts in that they are of higher pH and thus less corrosive. In comparison, the pH of 3% DABCO WT® catalyst at 25° C. is about 3.2. DABCO WT catalyst is a commercial delayed action catalyst for polyurethane foams recommended for use in systems where long-range package stability is required. DABCO WT catalyst is comprised of a blend of hydroxypropylimidazole and a diformic acid salt of triethylenediamine.

EXAMPLE 10

The same procedure as that of Example 9 was used except that the tertiary amine carbonates salts of Examples 5–7 were decomposed. The decomposition temperature range and the pH of the solutions before and after decomposition are listed in Table V below.

TABLE V

| Carbonate Salt of Example | Decomposition temp. range °C. | pH After Decomposition | pH Before Decomposition |
|---|---|---|---|
| 6 | 55–80 | 9.9 | 8.7 |
| 8 | 40–85 | 9.4 | 8.3 |

It is evident from Table V above that the carbonate salts decompose irreversibly to regenerate the more basic free tertiary amines.

The compounds of the present invention are advantageously useful as delayed action catalysts in the preparation of polyurethane, particularly in molded microcellular applications as in shoe soles and automotive bumper fascia, highly resilient foams and other machine parts.

The following examples illustrate some of the advantages of the compounds of the present invention over standard commercial catalysts.

EXAMPLE 11

Catalysts of this invention were evaluated in a flexible foam formulation of the composition shown in Table VI, using "hand mix" technique.

TABLE VI

| Component | pbw |
|---|---|
| Voranol ® 3010[1] | 100 |
| Methylene chloride | 20 |
| Silicone L6202[2] | 1.5 |
| Water | 3.6 |
| Catalyst | (as shown below) |
| Mondur ® T80[3] | 46.1 |
| Hood temperature, 82–83° F. | |

| Catalyst | Conc., pbw | | | |
|---|---|---|---|---|
| 50% T-9[4] | 0.6 | 0.8 | 0.6 | 0.8 |
| DABCO ® TL[5] | 0.4 | 0.4 | — | — |
| Cat. of Ex. 1 | — | — | 0.6 | 0.6 |
| Reactivity | | | | |
| Begin. of rise, secs | 16 | 15 | 15 | 15 |
| Rise time, secs | 115 | 100 | 112 | 110 |
| Hard gel, secs | 145 | 130 | 130 | 117 |
| Quality of foam | good | good | good | good |

[1]Voranol 3010 is a commercial polyether polyol of hydroxyl number 54.4–58.4; manufactured and sold by Dow Chemical Co.
[2]Silicone L-6202 is a commercial silicone surfactant; distributed by Union Carbide Corporation.
[3]Mondur TD-80 is an 80/20 mixture of 2,4- and 2,6-toluene diisocyanate, which has 48% NCO and an equivalent weight of 87; distributed by Mobay Chemical Co.
[4]T-9 is a trade name for stannous octoate sold by M & T Co.
[5]DABCO TL catalyst is a proprietary mixture of DABCO 33-LV defined in Table VII below and DABCO-T catalysts, both sold by Air Products and Chemicals, Inc. DABCO-T is N,N" trimethylhydroxy ethyl ethylene diamine.

From the data in Table VI it is evident that the catalysts of the present invention are advantageous in that they provide for the same cream time (beginning of rise) but with much shorter hard gel time. This is of considerable importance to the manufacturer since he can speed up his conveyor line and increase output. It should be noted that the active concentration of amine in both the control and experimental catalysts is the same, namely, 0.21 parts per 100 of polyol.

EXAMPLE 12

The same procedure was used as that in Example 11 above except that the formulation was changed to that shown in Table VII below:

TABLE VII

FLEXIBLE FOAM FORMULATION

| Component | pbw |
| --- | --- |
| Voranol 3010 | 100 |
| Water | 4.6 |
| Methylene chloride | 7.0 |
| Silicone L6202 | 1.2 |
| Catalyst | as shown below |
| Hylene TM[6] | 62.5 |

| Catalyst | Conc. pbw | | | | | | |
| --- | --- | --- | --- | --- | --- | --- | --- |
| T-9, 25% in DOP | 1.2 | 1.2 | 1.2 | 1.2 | 1.2 | 1.2 | 1.2 |
| DABCO ® 33-LV[7] | 0.1 | 0.15 | 0.2 | — | — | — | — |
| Cat. of Example 1 | — | — | — | 0.25 | 0.3 | 0.35 | 0.4 |
| Reaction Profile | | | | | | | |
| Beginning of rise, secs. | 11 | 10 | 8 | 14 | 13 | 14 | 12 |
| Hard gel, secs. | 124 | 115 | 90 | 132 | 127 | 116 | 113 |
| Rise time, secs. | 100 | 87 | 72 | 110 | 106 | 95 | 92 |
| Health bubbles | 100 | 87 | 72 | 110 | 106 | 95 | 92 |

[6]Hylene TM is an 80/20 mixture of 2,4- and 2,6-toluene diisocyanate sold by duPont.
[7]DABCO ® 33-LV catalyst is a 33% by weight solution of TEDA in dipropylene glycol; sold by Air Products and Chemicals, Inc.

From the data in Table VII it is apparent that good flexible foams with extended cream and gel time are obtained using the catalysts of the present invention. This is particularly desirable when using new foam machinery such as the Maxfoam machines.

EXAMPLE 13

Catalysts of this invention were evaluated in high resilient foam (H.R.) formulation listed in Table VIII below using the "hand mix" technique. The reactants were mixed by a high speed mixer for ten seconds, then poured into an aluminum tray having a surface temperature of 100°–110° F. (38°–43° C.). After the material formed as a hard gel, it was placed in an oven at 150° F. (66° C.) and the tack-free time was determined. Table IX below shows the reaction profiles of H.R. foams made at various catalyst levels.

TABLE VIII

| Component | pbw |
| --- | --- |
| [8]NIAX ® 32-10 | 100.0 |
| Distilled water | 3.3 |
| [9]Freon 11B | 6.0 |
| [10]Silicone L5309 | 2.0 |
| [11]T-12 | 0.005 |
| Amine Catalyst | as shown in Table IX |
| [12]TD1/PAP1 80/20 | 42.0 |

[8]NIAX 32-10 is a polyol having an average hydroxyl number of 32.5; sold by Union Carbide Corporation.
[9]Freon 11B is a trade name for fluorotrichloromethane; sold by du Pont.
[10]L-5309 is a brand of silicone surfactant; sold by Union Carbide Corporation.
[11]T-12 is dibutyl tin dilaureate.
[12]TD1/PAP1 is a mixture of 2,4 and 2,6 toluene diisocyanate isomers with a polymeric methylene bis-diphenyl isocyanate, the latter having an equivalent weight of 133 and containing 31.5% of NCD; sold by Upjohn Company.

TABLE IX

| Catalyst | Conc. in pph | | | | | | | |
| --- | --- | --- | --- | --- | --- | --- | --- | --- |
| DABCO ® 33-LV | 0.95 | 1.2 | 1.5 | — | — | — | — | — |
| Cat. of Example 1 Reaction Profile | — | — | — | 0.95 | 1.4 | 1.8 | 2.2 | 2.5 |
| Cream time, secs | 8 | 8 | 6 | 9 | 9 | 7 | 6 | 6 |
| Rise time, secs | 95 | 80 | 65 | 145 | 12 | 95 | 78 | 72 |
| Hard gel time, secs | 100 | 95 | 80 | 220 | 160 | 135 | 85 | 75 |
| Tack free time, secs | 20 | 18 | 15 | 15 | 15 | 10 | 8 | 6 |
| Quality of foam | poor, blistering on bottom and corners | dishing on bottom, blistering on side | good foam, fine cell structure | some blistering, fine cell structure | some bubbles, fine cell formation | slight dishing, fine cell structure | good, acceptable foam, fine structure | excellent foam, open cells |

It is evident from Table IX above that the catalysts of the invention provide for longer gel time, hence good flow, and at the same time form tack-free foams at 150° F. (66° C.) much faster than the usual commercial catalysts, thereby affording shorter demold time and increased productivity. It is also to be noted that the active ingredient at the highest level used in the tests of Table IX is the same, namely, 0.5 parts of active triethylene diamine per 100 parts of polyol.

The foregoing examples are illustrative of the properties and characteristics of the compounds of the present invention. These compounds could be used in formulations with other well-known amine or amine salt co-catalysts as well as with other organometallic co-catalysts such as antimony carboxylates, mercuric propionate and the like.

EXAMPLE 14

The tertiary amine carbonate salts were tested in a flexible foam formulation using the earlier described "hand mixing" techniques. The carbonate salts were compared to standard DABCO catalysts in presence of stannous octoate as the co-catalyst. The composition of the formulation and the reaction profiles obtained with the control and catalysts of this invention are shown on Table X below.

It is apparent from Table X that the carbonate salt provide for delaying cream by a factor of 2 while the gel is delayed by only 1.3 at a substantially lower level of amine catalyst. (See column 1, 3 and 5 of Table X.)

TABLE X

FORMULATION

| Premix | Multranol 7100 | 100 parts | Room Temp. 62° F. |
|---|---|---|---|
| | Water | 3.0 parts | Hood Temp. 58° F. |
| | Silicone L-540 | 1.0 parts | Reactant Temp. 23° C. |
| | Catalyst | As Shown | |
| | TDI 80/20 | 39.3 (107 index) | |

Concentration, parts per 359.8 parts of premix

| Catalyst | | | | | | | | | | |
|---|---|---|---|---|---|---|---|---|---|---|
| T-9 (Stannous Octoate) | 0.525 | 0.525 | 0.525 | 0.525 | 0.525 | 0.525 | 0.525 | 0.525 | 0.525 | 0.527 |
| DABCO ® 33LV | 1.05 | — | — | — | — | — | — | — | — | — |
| NIAX A-1 | 0.7 (0.872) | — | — | — | — | — | — | — | — | — |
| DABCO ® T | — | 1.2 | — | — | — | — | — | — | — | — |
| Cat. of Ex. 7 | — | — | 2.72 (0.6) | 2.71 (0.6) | — | — | — | — | — | — |
| Cat. of Ex. 4 | — | — | — | — | 2.96 (0.64) | 2.96 (0.64) | — | — | — | — |
| Cat. of Ex. 8 | — | — | — | — | — | — | 2.14 (0.856) | 2.14 (0.856) | — | — |
| Cat. of Ex. 5 | — | — | — | — | — | — | — | — | 3.0 (0.15) | 3.0 (1.05) |
| Cream time (secs.) | 8, 8 | 10 | 14 | 15 | 10 | 10 | 17 | 19 | 9 | 9 |
| Rise time (secs.) | 72–95 | 134–195 | 155 | 155–195 | 85–155 | 100–160 | 175–200 | 140–185 | 150–215 | 132–210 |
| Hard Gel (secs.) | 170 | 215 | 225 | 215 | 218 | 235 | 215 | 208 | 225 | 225 |

What is claimed is:
1. The triethylene diamine salt of carbonic acid.
2. The bis(dimethylaminoethyl) ether salt of carbonic acid.

* * * * *